(12) United States Patent
Masakazu

(10) Patent No.: US 9,707,115 B2
(45) Date of Patent: Jul. 18, 2017

(54) STENT DELIVERY SYSTEM

(71) Applicant: TERUMO KABUSHIKI KAISHA, Shibuya-ku (JP)

(72) Inventor: Shimoyama Masakazu, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 95 days.

(21) Appl. No.: 14/286,356

(22) Filed: May 23, 2014

(65) Prior Publication Data

US 2014/0257459 A1 Sep. 11, 2014

Related U.S. Application Data

(63) Continuation of application No. PCT/JP2013/050551, filed on Jan. 15, 2013.

(30) Foreign Application Priority Data

Feb. 15, 2012 (JP) ................. 2012-030027

(51) Int. Cl.
  *A61F 2/06* (2013.01)
  *A61F 2/966* (2013.01)
  *A61F 2/95* (2013.01)

(52) U.S. Cl.
  CPC ...... *A61F 2/966* (2013.01); *A61F 2002/9517* (2013.01)

(58) Field of Classification Search
  CPC .......................... A61F 2/966; A61F 2002/9517
  (Continued)

(56) References Cited

U.S. PATENT DOCUMENTS 4,106,508 A * 8/1978 Berlin ................ A61B 17/1227
  251/7
6,206,888 B1 * 3/2001 Bicek ........................ A61F 2/95
  606/108
(Continued)

FOREIGN PATENT DOCUMENTS

JP 2004-528066 A 9/2004
JP 2008-500090 A 1/2008
(Continued)

OTHER PUBLICATIONS

International Search Report (PCT/ISA/210) mailed on Apr. 16, 2013, by the Japanese Patent Office as the International Searching Authority for International Application No. PCT/JP2013/050551.
(Continued)

*Primary Examiner* — Amy R Weisberg
(74) *Attorney, Agent, or Firm* — Buchanan Ingersoll & Rooney PC

(57) ABSTRACT

In an operating unit constituting a stent delivery system, a protector for preventing an inner tube body from deforming is provided between a rack member and a containing groove guiding the rack member (so as to be movable. The protector, for example is a bellows shaped cylinder so as to be freely extendable and covers an outer circumferential side of the inner tube body. At the time of releasing a stent, the protector is compressed due to the movement of the rack member toward the proximal side and the inner tube body is prevented from deforming due to the protector, because an inner circumferential surface of the protector comes into contact with the inner tube body.

18 Claims, 6 Drawing Sheets

(58) Field of Classification Search
USPC .................................................. 623/1.11–1.35
See application file for complete search history.

(56) References Cited

U.S. PATENT DOCUMENTS

| | | | | |
|---|---|---|---|---|
| 6,514,261 B1* | 2/2003 | Randall | ..................... | A61F 2/95 604/528 |
| 6,599,296 B1* | 7/2003 | Gillick | ............... | A61B 17/3207 606/108 |
| 8,702,727 B1* | 4/2014 | Harrington | ............... | A61F 6/18 606/108 |
| 8,852,258 B2* | 10/2014 | Lubinski | ................. | A61F 2/966 604/134 |
| 8,888,834 B2* | 11/2014 | Hansen | ..................... | A61F 2/95 604/165.01 |
| 9,192,500 B1* | 11/2015 | Longo | .................... | A61B 90/00 |
| 2002/0004663 A1* | 1/2002 | Gittings | ................. | A61B 17/11 606/153 |
| 2002/0099431 A1 | 7/2002 | Armstrong et al. | | |
| 2003/0028236 A1* | 2/2003 | Gillick | ..................... | A61F 2/95 623/1.11 |
| 2003/0191516 A1* | 10/2003 | Weldon | ..................... | A61F 2/95 623/1.12 |
| 2004/0006380 A1* | 1/2004 | Buck | ....................... | A61F 2/966 623/1.11 |
| 2004/0097988 A1* | 5/2004 | Gittings | ................. | A61B 17/11 606/153 |
| 2005/0033343 A1 | 2/2005 | Chermoni | | |
| 2005/0080476 A1* | 4/2005 | Gunderson | ............... | A61F 2/95 623/1.11 |
| 2005/0090887 A1* | 4/2005 | Pryor | ....................... | A61F 2/95 623/1.11 |
| 2005/0149159 A1* | 7/2005 | Andreas | .................... | A61F 2/95 623/1.11 |
| 2006/0286145 A1* | 12/2006 | Horan | ....................... | A61F 2/95 424/426 |
| 2007/0100422 A1* | 5/2007 | Shumer | ..................... | A61F 2/95 623/1.11 |
| 2007/0118201 A1* | 5/2007 | Pappas | ..................... | A61F 2/95 623/1.11 |
| 2007/0156225 A1* | 7/2007 | George | ..................... | A61F 2/95 623/1.12 |
| 2007/0191865 A1* | 8/2007 | Pappas | ..................... | A61F 2/966 606/108 |
| 2008/0082159 A1* | 4/2008 | Tseng | ........................ | A61F 2/07 623/1.13 |
| 2008/0319524 A1* | 12/2008 | Yachia | ..................... | A61F 2/95 623/1.11 |
| 2010/0036472 A1* | 2/2010 | Papp | ......................... | A61F 2/95 623/1.11 |
| 2010/0125280 A1* | 5/2010 | Molloy | ..................... | A61F 2/95 606/108 |
| 2012/0296409 A1* | 11/2012 | Kawakita | ................ | A61F 2/915 623/1.12 |
| 2012/0330401 A1* | 12/2012 | Sugimoto | ............... | A61F 2/915 623/1.12 |
| 2013/0268049 A1* | 10/2013 | Munsinger | ................ | A61F 2/95 623/1.11 |
| 2013/0304189 A1* | 11/2013 | Shimoyama | ............ | A61F 2/966 623/1.12 |
| 2014/0088686 A1* | 3/2014 | Centola | ................. | A61F 2/2412 623/1.12 |
| 2015/0265445 A1* | 9/2015 | Weber | ..................... | A61F 2/966 623/1.12 |

FOREIGN PATENT DOCUMENTS

| | | |
|---|---|---|
| WO | WO 2011/081007 A1 | 7/2011 |
| WO | WO 2011/122444 A1 | 10/2011 |

OTHER PUBLICATIONS

Japanese Official Action issued Sep. 23, 2016, by the Japan Patent Office, in corresponding Japanese Patent Application No. 2014-500121 with English-language translation of Japanese Official Action(6 pages).

* cited by examiner

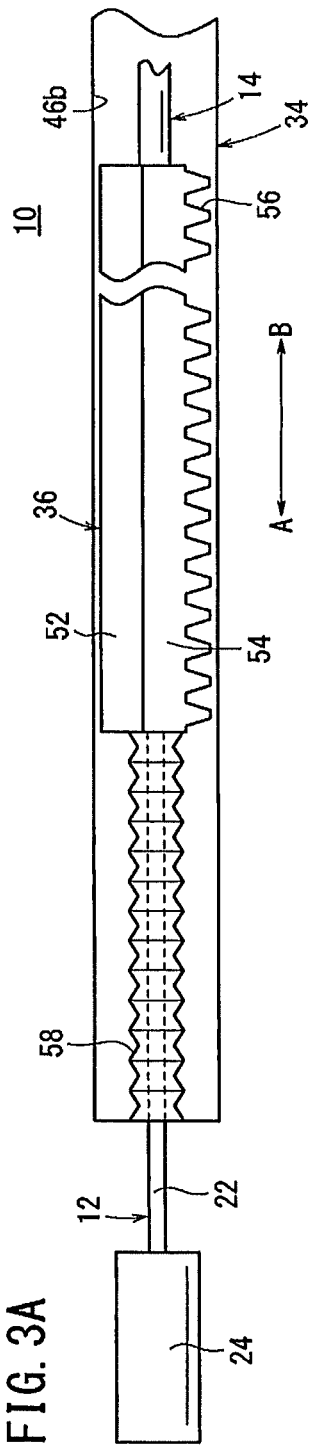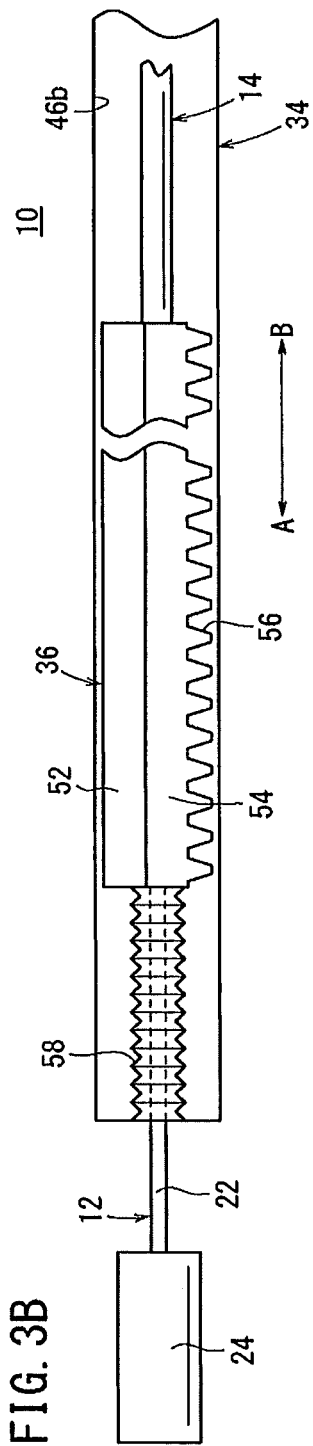

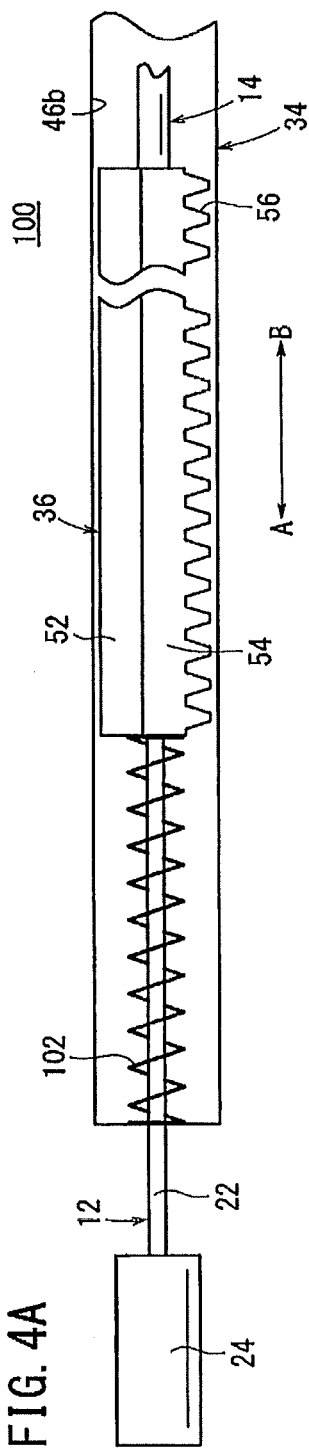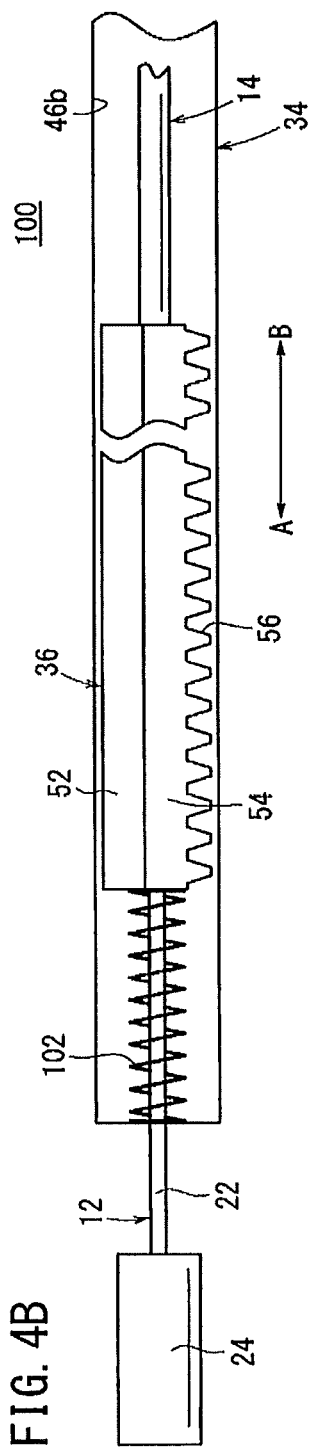

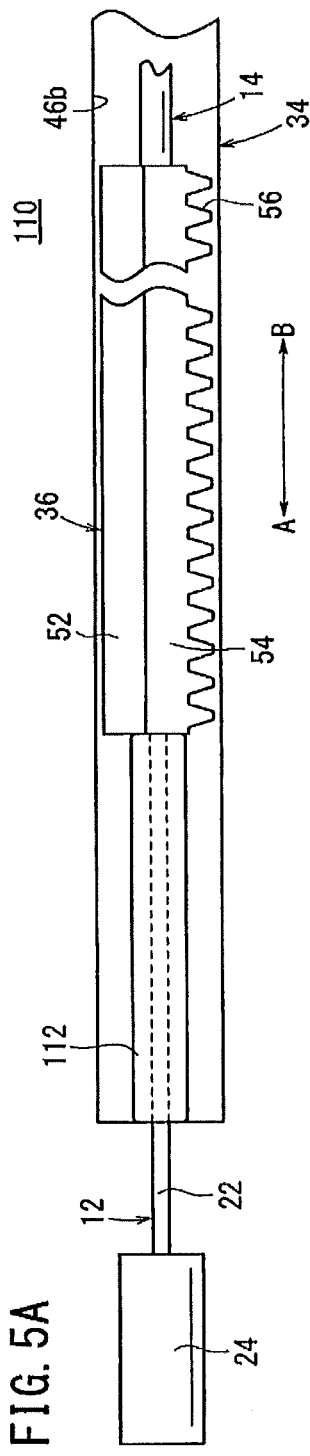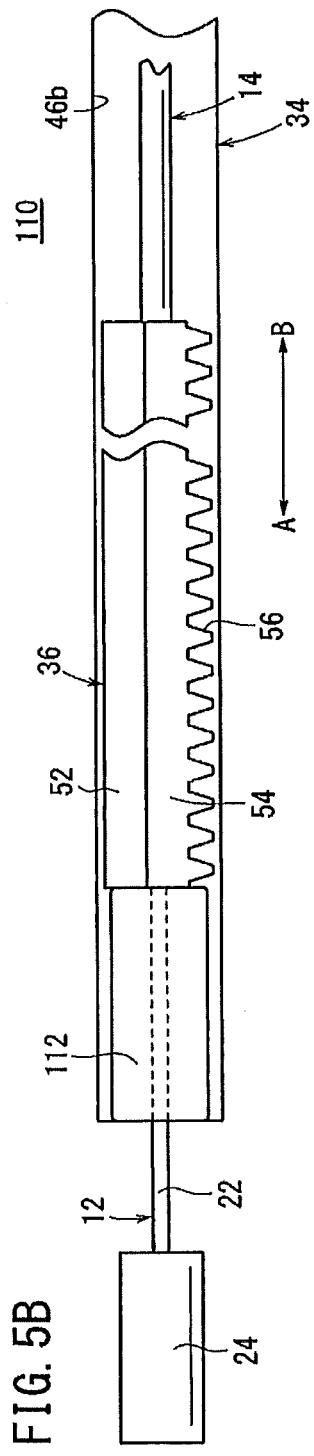

US 9,707,115 B2

STENT DELIVERY SYSTEM

CROSS REFERENCES TO RELATED APPLICATIONS

This application is a continuation of International Application No. PCT/JP2013/050551 filed on Jan. 15, 2013, and claims priority to Japanese Application No. 2012-030027 filed on Feb. 15, 2012, the entire content of both of which is incorporated herein by reference.

TECHNICAL FIELD

The present invention relates to a stent delivery system for delivering and indwelling a stent into a lumen of a living body such as a blood vessel.

BACKGROUND DISCUSSION

Conventionally, there have been cases where a stent, which is formed in the shape of a hollow cylinder having a multiplicity of openings in its side wall from a metallic wire or the like to be expanded in a lumen of a living body, such as a blood vessel, bile duct, trachea, esophagus and urethra, is used for improvement of a stenosed part or an obstructed part generated in the lumen of the living body.

In connection with the case of a self-expandable stent in which the stent itself has a self-expanding function, for example, there has been known a stent delivery system in which the stent is delivered into a living body in the state of being compressed and contained in a gap between an inner tube and an outer tube, and then the outer tube is retracted proximally so as to release the stent, whereby the stent is put indwelling in a desired lumen.

In Pamphlet of International Publication No. 2011/122444, a stent delivery system with this type of stent is proposed. The stent delivery system is provided with an operating unit by which an outer tube is advanced and retracted relative to an inner tube and releases the stent by moving the outer tube through the rack member meshed with a gear of a roller by the operator rotating the roller of the operating unit.

SUMMARY

A stent delivery system is described below by which an inner tube can be prevented from deforming while an outer tube is moved and a stent can be reliably put indwelling in a desired part in a lumen of a living body.

There is provided a stent delivery system including: an inner tube; a stent which is compressed toward a center axis and disposed on a distal side of the inner tube at the time of insertion into a lumen of a living body, and which can be restored into its pre-compression shape by expanding outward when put indwelling in the lumen of the living body; an outer tube which can contain the stent in its lumen by being disposed on an outer surface side of the inner tube, and can release the stent to the exterior by moving proximally relative to the inner tube; and an operating unit for moving the outer tube in an axial direction relative to the inner tube.

The operating unit includes a housing, and a protector for protecting an outer circumferential side of the inner tube which is connected to the housing is provided between the proximal end of the inner tube and the proximal end of the outer tube.

Conventionally, there have been cases where stress is exerted on the inner tube from the outer tube when the outer tube is moved toward the proximal side relative to the inner tube by operating an operating unit for releasing a stent. In the stent delivery system, by providing a protector for protecting an outer circumferential side of the inner tube, which is connected to the housing, between the proximal end of the inner tube and the proximal end of the outer tube, the inner tube is prevented from deforming by bringing the protector, which is provided on the outer circumferential side of the inner tube, into contact with the inner tube even when the stress is exerted on the inner tube from the outer tube.

Accordingly, the outer tube can be reliably prevented from malfunctioning due to the deformation of the inner tube and the stent can be reliably put indwelling in a desired part in a lumen of a living body.

BRIEF DESCRIPTION OF DRAWINGS

FIG. 3A is a partially omitted enlarged configuration view showing the vicinity of a proximal end of an operating unit shown in FIG. 2 and FIG. 3B is a partially omitted enlarged configuration view showing a state where an outer tube body of FIG. 3A is moved toward the proximal side.

FIG. 4A is a partially omitted enlarged configuration view showing the vicinity of a proximal end of an operating unit in a stent delivery system in which a protector according to a first modification example is used and FIG. 4B is a partially omitted enlarged configuration view showing a state where the outer tube body of FIG. 4A is moved toward the proximal side.

FIG. 5A is a partially omitted enlarged configuration view showing the vicinity of a proximal end of an operating unit in a stent delivery system in which a protector according to a second modification example is used and FIG. 5B is a partially omitted enlarged configuration view showing a state where the outer tube body of FIG. 5A is moved toward the proximal side.

DETAILED DESCRIPTION

Figure 1:
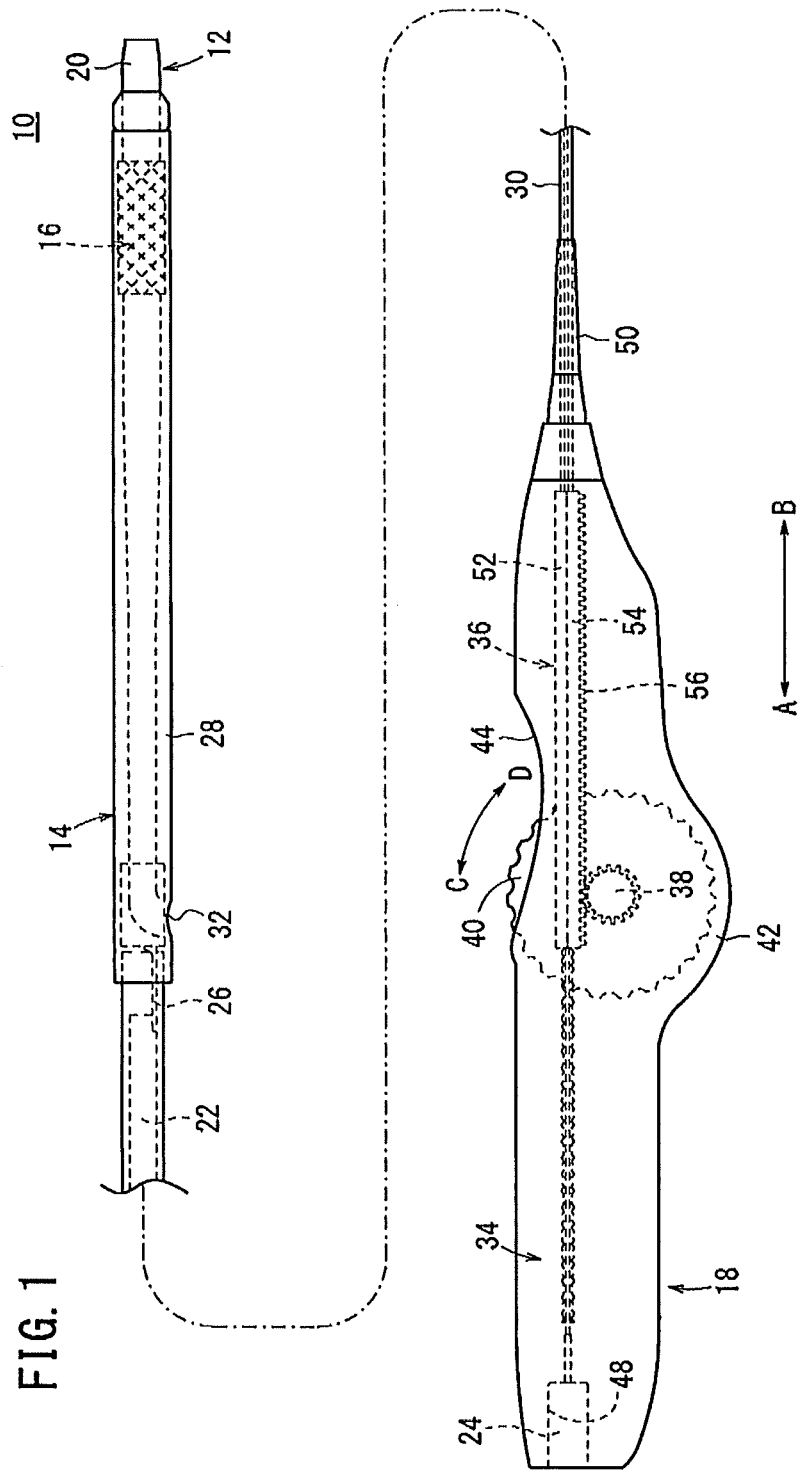
FIG. 1 is a general configuration view of a stent delivery system.

As shown in FIG. 1, this stent delivery system 10 includes: an inner tube body (inner tube) 12 formed in a tubular shape; an outer tube body (outer tube) 14 disposed on the outer circumference side of the inner tube body 12; an expandable stent 16 contained between the inner tube body 12 and the outer tube body 14; and an operating unit 18 for moving the outer tube body 14 relative to the inner tube body 12.

In FIG. 1, the left side of the inner tube body 12 and the outer tube body 14 is referred to as a "proximal end (rear end)" side (direction of arrow A), and the right side of the inner tube body 12 and the outer tube body 14 is referred to as a "distal end" side (direction of arrow B), the same applying also to the other figures.

As shown in FIG. 1, the inner tube body 12 includes: a first distal tube 20 formed with a guide wire lumen in which a guide wire is inserted into and passes through (positioned in); a first proximal tube 22 connected through a connecting member 26 to the proximal side (the direction of arrow A) of the first distal tube 20; and a connector 24 connected to the proximal end of the first proximal tube 22.

This inner tube body 12 is composed of tubular bodies, in which the distal ends and proximal ends of the first distal tube 20 and the first proximal tube 22 are respectively open, and the distal end of the first distal tube 20 is disposed so as to protrude beyond the distal end of the outer tube body 14. The above-mentioned guide wire is used, for example, for guiding the stent delivery system 10 to a lesion in a lumen of a living body.

The inner tube body 12 has a structure in which the proximal end of the first distal tube 20 and the distal end of the first proximal tube 22 are connected to each other, through the connecting member 26, inside the outer tube body 14. In addition, the first proximal tube 22 has a lumen penetrating therethrough from the distal end to the proximal end of the first proximal tube 22. A liquid such as physiological saline is injected into the lumen via the connector 24.

The outer tube body 14 is composed of tubular bodies and has a second distal tube 28 in which the first distal tube 20 of the inner tube body 12 is disposed and a second proximal tube 30 which is connected to the proximal side (the direction of arrow A) of the second distal tube 28 and in which the first proximal tube 22 is disposed. The distal end of the second distal tube 28 functions as a release port at the time of indwelling the stent 16 into a lesion in a lumen of a living body, and functions also as a containing port at the time of recovering the stent 16 again, having been released to an intermediate extent.

In addition, on the proximal end of the second distal tube 28, there is formed a guide wire leading-out hole 32 opened so as to establish communication between the inner lumen of the second distal tube 28 and the exterior. The guide wire leading-out hole is provided so that it can communicate with the opening of the guide wire lumen of the first distal tube 20 provided inside the second distal tube. Through the guide wire leading-out hole 32, the guide wire is inserted into (positioned in) and passes through the guide wire lumen of the inner tube body 12.

The stent 16 is formed in the shape of a substantially cylindrical mesh having a multiplicity of openings. The stent 16 is a self-expandable stent which is disposed between the second distal tube 28 of the outer tube body 14 and the first distal tube 20 of the inner tube body 12 in the state of being compressed radially inward toward the center axis at the time of insertion into a lumen of a living body, and which, by being released via the distal end of the outer tube body 14 into a lesion in the lumen of the living body, can be expanded radially outward to be restored into its pre-compression shape.

Figure 2:
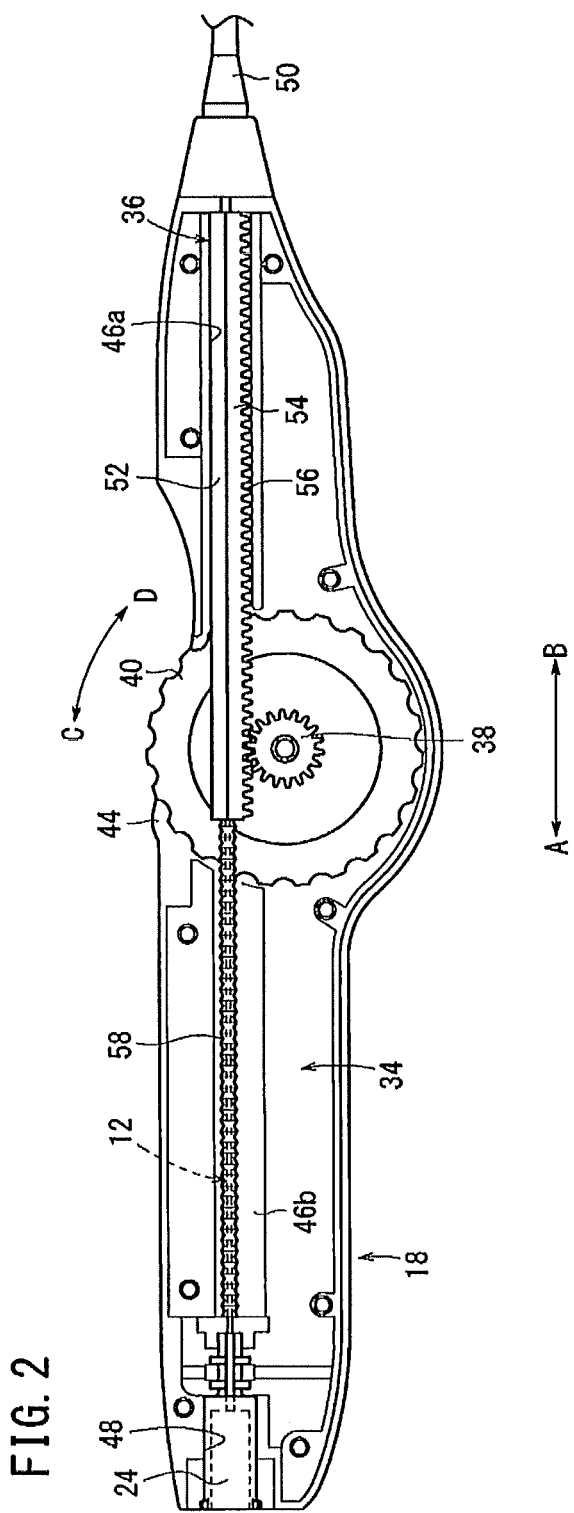
FIG. 2 is a side view of the inside of an operating unit shown in FIG. 1.

As shown in FIGS. 1 and 2, the operating unit 18 includes a housing 34, a rack member (connector) 36 connected to the outer tube body 14 and contained inside the housing 34, and a rotary roller 40 having a gear 38 meshed with the rack member 36 and rectilinearly moving the rack member 36.

The housing 34 is round-shaped at its central portion. A roller containing section 42 capable of containing the rotary roller 40 is formed in the substantially central portion of the housing. Part of the rotary roller 40 is exposed to the exterior through a roller hole 44 formed in the roller containing section 42. The rotary roller 40 is rotatably supported by a pair of bearings (not shown) formed on an inner wall of the housing 34.

In addition, the housing 34 is formed with a set of containing grooves 46a and 46b in which the rack member 36 is contained and retained so as to be movable in the axial direction (in the directions of arrows A and B). A connector containing section 48 which contains the connector 24 is formed on the proximal side (the direction of arrow A) relative to the containing groove 46b. The connector 24 is fixed to the housing 34 by being contained in the connector containing section 48. As a result, the proximal end of the first proximal tube 22 constituting the inner tube body 12 is fixed to the operating unit 18 through the connector 24.

Meanwhile, a distal nozzle 50, by which the second proximal tube 30 of the outer tube body 14 is slidably retained, is mounted on the distal end of the housing 34. The distal nozzle 50 is formed with a through-hole (not shown) where the second proximal tube 30 is inserted into (positioned in) and passes through.

The rack member 36 is composed of a set of the first and second block bodies 52 and 54 which are formed in straight shapes and in substantially symmetrical shapes. The proximal end of the second proximal tube 30 in the outer tube body 14 is fixed by being interposed between the first block body 52 and the second block body 54. In this case, the inner tube body 12 is freely movable inside the outer tube body 14.

Then, the rack member 36, being composed of the first and second block bodies 52 and 54, is inserted into (positioned in) the containing grooves 46a and 46b inside the housing 34, whereby the rack member is retained in the state of being rectilinearly movable toward the distal side and the proximal side (in the directions of arrows A and B) of the housing 34.

The second block body 54 is provided inside the housing 34 so as to face the rotary roller 40, and its side surface facing the rotary roller 40 is provided with a plurality of tooth portions 56 defined by projections and recesses arranged along the axial direction (in the directions of arrows A and B).

Furthermore, as shown in FIGS. 1 to 3B, the protector 58, being formed in a bellows-like or bellows-shaped cylinder made of a resin material, is provided between the proximal end of the inner tube body 12 and the proximal end of the outer tube body 14, and more specifically, between the proximal end of the rack member 36 and the proximal end of the containing groove 46b. The protector 58 is formed to be freely extendable in the axial direction (directions of arrows A and B), the distal end of the protector comes into contact with the proximal end of the first and second block bodies 52 and 54, and the proximal end of the protector comes into contact with the inner wall which is the proximal end of the containing groove 46b (refer to FIGS. 3A and 3B). In other words, the distal end of the protector 58 is connected to and in contact with the proximal end of the rack member 36. In one aspect, the distal end of the protector 58 may be fixed to the proximal end of the rack member 36. That is, the protector 58 is interposed between the rack member 36 and the containing groove 46b so as to connect them. In addition, the first proximal tube 22 constituting the inner tube body 12 is inserted into (positioned in) and passes through inside the protector 58 along the axial direction of the substantial central portion.

A material and a shape of the protector 58 is selected such as to have a small elastic force relative to the thrust that is generated by the rack member 36 moving toward the proximal side (in the direction of arrow A).

The rotary roller 40 is formed, for example, in a wheel shape, and a pair of rotary shafts provided in the center portion of the rotary roller 40 is respectively inserted in (positioned in) the bearings (not shown) of the housing 34. In addition, the side surface of the rotary roller 40 is provided with a gear 38 having the rotary shaft as a center and is meshed with a tooth portion 56 of the rack member 36. Moreover, with the rotary roller 40 rotated, the rack member 36 is rectilinearly moved along the containing grooves 46a and 46b. Part of the outer circumferential portion of the rotary roller 40 is exposed to the exterior through a roller hole 44 of the housing 34, and the operator rotates the rotary roller 40 through the exposed portion.

In the operating unit 18 described above, for example, by the rotation of the rotary roller 40 in a predetermined direction (in the direction of arrow C in FIGS. 1 and 2) relative to the housing 34 performed by the operator, the rack member 36 moves to the connector 24 side (in the direction of arrow A) along the containing grooves 46a and 46b inside the housing 34. This is attended by movement (retraction) of the outer tube body 14 toward the proximal side (direction of arrow A) of the housing 34. As a result, the stent 16 is released from the distal end of the outer tube body 14.

In contrast, after the stent 16 is released to an intermediate extent, the rotary roller 40 is rotated in the direction opposite to the above-mentioned direction (in the direction of arrow D in FIGS. 1 and 2). By this operation, the rack member 36 is moved in the direction (in the direction of arrow B) away from the connector 24 along the containing grooves 46a and 46b. This is attended by movement (advancement) of the outer tube body 14 toward the distal side (in the direction of arrow B) relative to the inner tube body 12, whereby the stent 16 is again contained in the inside of the outer tube body 14.

The stent delivery system 10 is basically configured as described above. Now, the operation and effect of the stent delivery system will be described below.

First, a state is assumed in which the guide wire is inserted into (located in) a lumen of a living body (for example, a blood vessel) and its distal end has been put indwelling at a lesion in the lumen of the living body in advance. Moreover, the operator connects a liquid injector (not shown) to the connector 24 disposed at the proximal end of the operating unit 18 and injects a liquid such as physiological saline from the liquid injector into the connector 24. As a result, the liquid flows to the distal side of the inner tube body 12 and the outer tube body 14 (in the direction of arrow B). Then, the liquid having reached the distal end is ejected from the distal ends of the inner tube body 12 and the outer tube body 14, whereby air venting (priming) of the inside of the inner tube body 12 and the outer tube body 14 in vitro is completed.

Next, the proximal end of the guide wire exposed in vitro is inserted into and passes through the distal end of the inner tube body 12 into the guide wire lumen and the inner tube body 12 and the outer tube body 14 are gradually advanced along the guide wire into the lumen of the living body.

After the arrival of the distal end of the outer tube body 14 in the lesion is confirmed by a contrast marker not shown, the rack member 36 is moved to the proximal side (in the direction of arrow A) in the housing 34, accompanied by rotation of the gear 38 with the rotary roller 40 rotated in a predetermined direction (in the direction of arrow C). This is attended by gradual movement of the outer tube body 14 toward the proximal side of the operating unit 18. In addition, at the same time, the protector 58 is gradually compressed so as to being pressed and crushed (the distal end of the protector 58 is moved in the axial direction towards the proximal end of the inner tube 12) in the axial direction (in the direction of arrow A) in a state where the first proximal tube 22 of the inner tube body 12 is inserted into (positioned in) and passes through the protector 58. In other words, the axial extension dimension of protector 58 is reduced as can be seen in comparison of FIGS. 3A and 3B with the movement of the rack member to the proximal side (in the direction of arrow A) in the housing 34, accompanied by rotation of the gear 38 with the rotary roller 40 rotated in a predetermined direction (in the direction of arrow C).

As a result, the stent 16 contained inside the outer tube body 14 starts being gradually exposed, starting from its distal portion; simultaneously, the stent starts being expanded radially outward. Then, the stent 16 comes into the state of being completely exposed from (outside of) outer tube body 14, whereby the stent is put indwelling in the lesion in the state of being expanded in the cylindrical shape.

In addition, at the time of releasing the stent 16 in the above mentioned manner, the rack member 36 is moved toward the proximal side (in the direction of arrow A) under the rotating action of the rotary roller 40. However, there have been cases where stress is exerted on the inner tube body 12 from the rack member 36 or the outer tube body 14 caused by, for example, distortions or curves of the inner tube body 12, fluctuation of the rack member 36 in the containing groove 46b during the movement, or the like.

Even in such a case, since deformation of the first proximal tube 22 of the inner tube body 12 in the radial direction due to the stress is restricted by an inner circumferential surface of the protector 58 covering (protecting) the outer circumferential side, the inner tube body 12 can be reliably prevented from buckling. As a result, it is possible for the stent 16 to be reliably put indwelling into a lesion in a lumen of a living body.

As described above, in the first embodiment, in the operating unit 18 constituting the stent delivery system 10, by providing the protector 58 formed to have a bellows-like or bellow-shaped cylinder between the proximal end of the containing groove 46b and the proximal end of the rack member 36 which are formed in the housing 34 so as to cover (protect) the first proximal tube 22 of the inner tube body 12, the inner tube body 12 is prevented from deforming by bringing the cylinder-like or cylinder shaped protector 58 provided in the outer circumferential side of the inner tube body 12 into contact with the inner tube body even in the case where the stress caused by, for example, distortions or curves of the inner tube body 12, fluctuation of the rack member 36 in the containing groove 46b during the movement, or the like is exerted on the inner tube body 12 at the time of retracting the rack member 36 toward the proximal side (in the direction of arrow A) under the rotating action of the rotary roller 40 to release the stent 16.

As a result, the outer tube body 14 can be reliably prevented from malfunctioning due to the deformation of the inner tube body 12 and the stent 16 can be reliably put indwelling in a desired part in a lumen of a living body.

That is, the inner tube body 12 is prevented from deforming by providing the cylinder-like or cylinder shaped protector 58 on the outer circumferential side of the inner tube body 12, thereby restricting the deformable space of the inner tube body.

In addition, instead of installing the bellows-like or bellows shaped protector 58 described above, a spiral-like or spiral shaped protector 102 may be used as in a stent delivery system 100 shown in FIGS. 4A and 4B, and a protector 112 formed in, for example, a solid cylindrical shape may be used as in a stent delivery system 110 shown in FIGS. 5A and 5B.

The protector 102 according to a first modification example is formed by winding a wire material formed from a resin material in a spiral shape to be freely extendable in the axial direction (in the directions of arrows A and B). A material and a shape of the protector 102 is selected such as to have a small elastic force relative to the thrust that is generated by the rack member 36 moving toward the proximal side (in the direction of arrow A). The distal end of the protector 102 is disposed so as to come into contact with the proximal end of the rack member 36 and the proximal end of the protector 102 is disposed so as to come into contact with the inner wall of the proximal end in the containing groove 46b. That is, the distal end of the protector 102 is connected to and in contact with the proximal end of the rack member 36. In one aspect, the distal end of the protector 102 may be fixed to the proximal end of the rack member 36.

With the movement of the rack member 36 toward the proximal side (in the direction of arrow A) from the state shown in FIG. 4A, the protector 102 pressed by the proximal end of the rack member 36 is gradually compressed to the proximal side (in the direction of arrow A) by being pressed and crushed (compressed) and the deformation of the first proximal tube 22 of the inner tube body 12 inserted into (positioned in) and passing through the protector 102 is restricted by the inner circumferential surface of the protector 102, whereby the inner tube body 12 is reliably prevented from deforming (buckling). In other words, the axial extension dimension of protector 102 is reduced as can be seen in comparison of FIGS. 4A and 4B with the movement of the rack member to the proximal side (in the direction of arrow A) in the housing 34, accompanied by rotation of the gear 38 with the rotary roller 40 rotated in a predetermined direction (in the direction of arrow C). Accordingly, the outer tube body 14 can be reliably prevented from malfunctioning due to the deformation such as the buckling of the inner tube body 12 and the stent 16 can be reliably put indwelling in a desired part in a lumen of a living body.

In addition, the protector 112 according to a second modification example is formed from a resin material in a cylindrical shape. The distal end of the protector is provided so as to come into contact with the proximal end of the rack member 36 and the proximal end of the protector is provided so as to come into contact with the inner wall of the proximal end in the containing groove 46b. The distal end of the protector 112 is connected to and in contact with the proximal end of the rack member 36. In one aspect, the distal end of the protector 112 may be fixed to the proximal end of the rack member 36. The protector 112 is provided to be freely extendable in the axial direction (in the directions of arrows A and B) and is formed to be expansive in diameter by being compressed in the axial direction. A material of the protector 112 is selected such as to have a small elastic force relative to the thrust that is generated by the rack member 36 being moved toward the proximal side (in the direction of arrow A). Specifically, a sponge, a rubber, urethane and the like are preferable.

In addition, the first proximal tube 22 of the inner tube body 12 is inserted into (positioned in) and passes through the center portion of the protector 112 along the axial direction.

As the rack member 36 moves toward the proximal side (in the direction of arrow A) from the state shown in FIG. 5A, the protector 112 pressed by the proximal end of the rack member 36 is gradually pressed and crushed (compressed) to the proximal side (in the direction of arrow A) (compressed in an axial direction towards the proximal end of the inner tube 12), and at the same time, the diameter of the protector is gradually expanded radially outward. In other words, the axial extension dimension of protector 112 is reduced as can be seen in comparison of FIGS. 5A and 5B with the movement of the rack member to the proximal side (in the direction of arrow A) in the housing 34, accompanied by rotation of the gear 38 with the rotary roller 40 rotated in a predetermined direction (in the direction of arrow C). Accordingly, the deformation of the inner tube body 12 inserted into (positioned in) and passing through the protector 112 is restricted by the protector 112 and the inner tube body 12 is reliably prevented from buckling. Accordingly, the outer tube body 14 can be prevented from malfunctioning due to the deformation such as the buckling of the inner tube body 12 and the stent 16 can be reliably put indwelling at a desired part in a lumen of a living body.

Figure 6A:
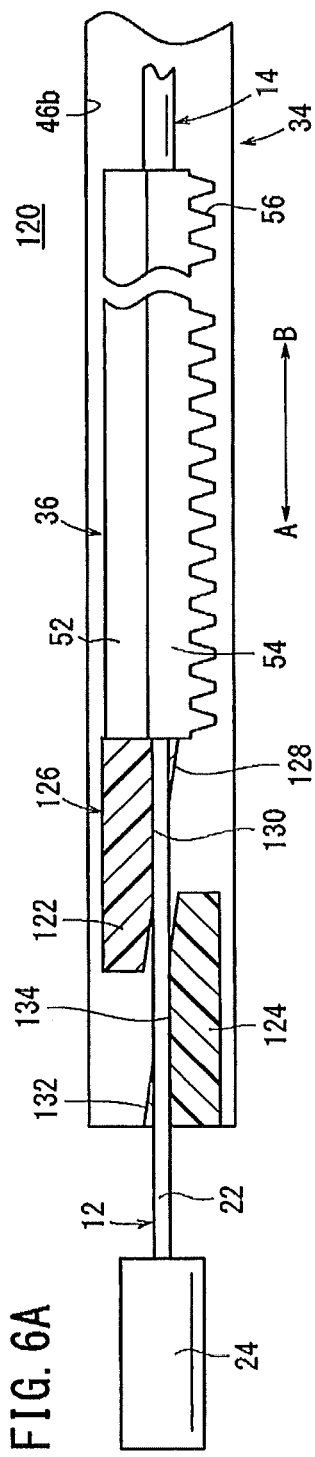
FIG. 6A is a partially omitted enlarged configuration view showing the vicinity of a proximal end of an operating unit in a stent delivery system in which a protector according to a third modification example is used and FIG. 6B is a partially omitted enlarged configuration view showing a state where the outer tube body of FIG. 6A is moved toward the proximal side.
Figure 6B:
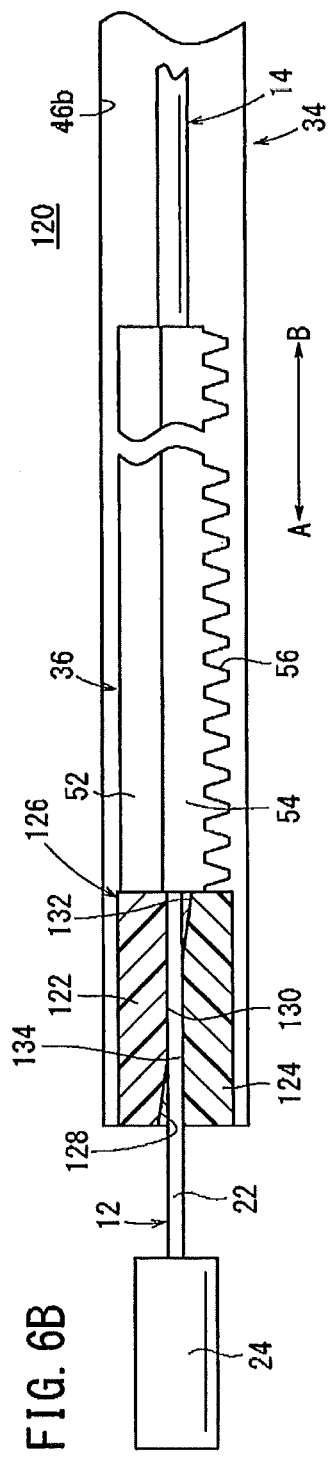

Meanwhile, instead of the protector 58 described above, as a stent delivery system 120 shown in FIGS. 6A and 6B, a protector 126 formed of two first and second slide members 122 and 124, both being provided between the proximal end of the inner tube body 12 and the proximal end of the outer tube body 14, may be used. More specifically, a protector 126 may be used, which is composed of a first slide member 122, being connected to the proximal end of the rack member 36 and a second slide member 124, being connected to the proximal end of the containing groove 46b.

In the protector 126 according to a third modification example, the first and second slide members 122 and 124 are formed from a resin material in a block shape. Moreover, the first slide member 122 is disposed upward relative to the inner tube body 12 and the second slide member 124 is disposed downward relative to the inner tube body 12.

A lower surface of the first slide member 122 has a first inclined surface 128 which is gradually inclined upward toward the direction (proximal side) away from the rack member 36 and a first groove portion 130 enclosing the inner tube body 12 is formed in the center of the first inclined surface 128 in a straight line. The first groove portion 130 is formed along the longitudinal direction (in the directions of arrows A and B) of the first slide member 122.

An upper surface of the second slide member 124 has a second inclined surface 132 which is gradually inclined downward toward the rack member 36 side (distal side) and a second groove portion 134 enclosing the inner tube body 12 is formed in the center of the second inclined surface 132 in a straight line. The second groove portion 134 is formed (positioned) along the longitudinal direction (in the directions of arrows A and B) of the second slide member 124. In addition, the inclined angle of the second inclined surface 132 is set to be substantially the same as that of the first inclined surface 128.

In the stent delivery system 120, in the state where the stent 16 is contained inside (located in) the outer tube body 14, as shown in FIG. 6A, the proximal end of the first slide member 122 and the distal end of the second slide member 124 are disposed so as to overlap each other in the axial direction by a predetermined length. In addition, part of the inner tube body 12 between the proximal end of the rack member 36 and the proximal end of the containing groove 46b is retained by the first groove portion 130 of the first slide member 122 and the rest of the inner tube body 12 is retained by the second groove portion 134 of the second slide member 124.

In the stent delivery system 120, as the rack member 36 moves toward the proximal side (in the direction of arrow A) from the state shown in FIG. 6A, the first slide member 122 pressed by the proximal end of the rack member 36 is gradually moved to the second slide member 124 side (in the direction of arrow A). Accordingly, the first inclined surface 128 and the second inclined surface 132 gradually approach each other. Moreover, with the movement of the first slide member 122 above the second slide member 124, the inner tube body 12 comes into a state of being retained from top and bottom by the first and second slide members 122 and 124.

That is, the inner tube body 12 between the proximal end of the rack member 36 and the proximal end of the containing groove 46b is retained by at least either the first slide member 122 or the second slide member 124 which constitutes the protector 126. Therefore, even when the stress is exerted on the inner tube body 12 accompanied by the movement of the rack member 36, the deformation of the inner tube body 12 is restricted by the protector 126 and the inner tube body 12 is reliably prevented from buckling. Accordingly, the outer tube body 14 can be reliably prevented from malfunctioning due to the deformation of the inner tube body 12 and the stent 16 can be reliably put indwelling in a desired part in a lumen of a living body.

The above-described stent delivery systems 10, 100, 110, and 120 have configurations where the distal ends of the protectors 58, 102, 112, and 126 are brought into contact with the proximal end of the rack member 36 and the protectors 58, 102, 112, and 126 are pressed when the rack member 36 is moved toward the proximal side (in the direction of arrow A). However, the configuration of the stent delivery system is not restricted thereto, and for example, other members (connectors) fixed to the rack member 36 may be further provided on the proximal side (in the direction of arrow A) of the rack member 36 and the protectors 58, 102, 112, and 126 may be provided between the other members and the containing groove 46b.

In addition, in the above-described description, the stent delivery system is configured such that the rack member 36 is movable along the axial direction (in the directions of arrows A and B) of the housing 34 by rotating the rotary roller 40. However, instead of providing the rotary roller 40, the stent delivery system may be configured such that the rack member 36 or the other members are movable by providing an operation lever which is exposed to the outside of the housing 34 and connected to the rack member 36 or the other members and by rectilinearly operating the operation lever.

The detailed description above describes a stent delivery system. The stent delivery system is disclosed by way of example. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
   an inner tube;
   a stent which is compressed toward a center axis and disposed on a distal side of the inner tube as the stent is inserted into a lumen of a living body, and which can be restored into a pre-compression shape by expanding outward as the stent is indwelled in the lumen of the living body;
   an outer tube disposed on an outer surface side of the inner tube, and configured to release the stent to the exterior by moving proximally relative to the inner tube;
   an operating unit for moving the outer tube in an axial direction relative to the inner tube;
   wherein the operating unit includes a housing;
   a protector different from the housing, the protector being a longitudinally extending cylinder that is axially expandable and contractable, the cylinder possessing an outer diameter that varies along a longitudinal extent of the cylinder so that spaced apart portions of the cylinder possess a relatively larger outer diameter and spaced apart portions of the cylinder possess a relatively smaller outer diameter less than the relatively larger outer diameter, the relatively larger outer diameter portions and the relatively smaller outer diameter portions alternating with one another along the longitudinal extent of the cylinder; and
   a connection body possessing a proximal-most end and a distal-most end, the outer tube being connected to the distal-most end of the connection body, the connection body including a tooth portion;
   a rotational member possessing a gear in meshing engagement with the tooth portion so that rotation of the rotational member produces axial movement of the tooth portion and the outer tube;
   wherein a distal end of the protector is directly connected to the proximal-most end of the connection body;
   wherein the housing includes a plurality of containing grooves in which the connection body is retained so as to be movable in the axial direction; and
   wherein the protector is provided between a proximal end of the connection body and a proximal end of one of the containing grooves.

2. The stent delivery system according to claim 1, wherein the protector covers the outer circumferential side of the inner tube.

3. The stent delivery system according to claim 1, wherein the protector is configured to be freely deformable in the axial direction when the outer tube is moved along the axial direction.

4. The stent delivery system according to claim 1, wherein the protector is configured to apply an elastic force which is less than a thrust generated by the outer tube moving toward the proximal side.

5. The stent delivery system according to claim 1, wherein a distal end of the protector is moved toward a proximal end of the protector when the outer tube or the connection body to which the outer tube is connected is moved in an axial direction relative to the inner tube.

6. A stent delivery system comprising:
   an inner tube possessing a proximal end and a distal end;
   an outer tube possessing a proximal end and a distal end, and operably connected to a tooth portion so that the outer tube and the tooth portion move together;
   a stent positioned between an outer surface of the distal end of the inner tube and an inner surface of the distal end of the outer tube in a collapsed state of the stent, the stent being configured to expand radially outwardly from the collapsed state by moving the outer tube proximally relative to the inner tube;
   a rotational member possessing a gear in meshing engagement with the tooth portion so that rotation of the rotational member produces axial movement of the tooth portion and the outer tube;
   a housing possessing an inner surface;
   a protector different from the housing and different from the rotational member, the protector being between the proximal end of the inner tube and the proximal end of the outer tube, the protector possessing an outer surface and the inner tube being positioned inside the protector;

the protector possessing an inner surface facing the outer surface of the inner tube, and the outer surface of the protector being spaced from the inner surface of the housing;

the protector being a longitudinally extending cylinder that is axially expandable and contractable, the cylinder possessing an outer diameter that varies along a longitudinal extent of the cylinder so that spaced apart portions of the cylinder possess a relatively larger outer diameter and spaced apart portions of the cylinder possess a relatively smaller outer diameter less than the relatively larger outer diameter, the relatively larger outer diameter portions and the relatively smaller outer diameter portions alternating with one another along the longitudinal extent of the cylinder;

a connection body possessing a proximal-most end and a distal-most end, the outer tube being connected to the distal-most end of the connection body, the connection body including the tooth portion; and wherein a distal end of the protector is directly connected to the proximal-most end of the connection body.

7. The stent delivery system according to claim 6, wherein the protector is spiral shaped along an axial direction of the protector.

8. The stent delivery system according to claim 6, wherein the protector is cylindrically shaped.

9. The stent delivery system according to claim 6, wherein the protector comprises at least two slide members positioned between the proximal end of the inner tube and the proximal end of the outer tube.

10. The stent delivery system according to claim 9, wherein the at least two slide members are movable relative to each other.

11. The stent delivery system according to claim 6, wherein a distal end of the protector moves toward the proximal end of the inner tube when the outer tube is moved proximally relative to the inner tube.

12. The stent delivery system according to claim 6, wherein the distal end of the protector is axially moved towards the proximal end of the protector when the connection body is moved proximally in an axial direction.

13. The stent delivery system according to claim 6, wherein the distal end of the outer tube is axially moved towards the proximal end of the outer tube when the connection body is moved proximally in an axial direction such that the stent expands radially outwardly from the collapsed state.

14. A stent delivery system comprising:
an inner tube possessing a proximal end and a distal end;
an outer tube possessing a proximal end and a distal end;
a stent positioned between an outer surface of the distal end of the inner tube and an inner surface of the distal end of the outer tube in a collapsed state of the stent, the stent being configured to expand radially outwardly from the collapsed state by moving the outer tube proximally relative to the inner tube in an axial direction;
an operating unit including a housing, a connection body and a rotational member;
a protector between a proximal-most end of the inner tube and the proximal end of the outer tube, the inner tube being positioned inside the protector;
the connection body possessing a distal-most end and a proximal-most end, the outer tube being connected to the distal-most end of the connection body, the connection body including a tooth portion such that the outer tube and the connection body are operably connected, and a distal end of the protector being directly connected to the proximal-most end of the connection body, the connection body being movable in the axial direction relative to the housing of the operating unit;
an axial dimension of the protector being reduced when the connection body is moved axially towards the proximal-most end of the inner tube;
the rotational member possessing a gear in meshing engagement with the tooth portion, the rotational member being rotatably mounted at the housing to rotate about a rotational axis perpendicular to the axial direction so that rotation of the rotational member about the rotational axis moves the connection body and the outer tube in the axial direction; and
the protector being comprised of a longitudinally extending cylindrical wall possessing a distal end and a proximal end;
wherein the housing includes a plurality of containing grooves in which the connection body is retained so as to be movable in the axial direction; and
wherein the protector is provided between the proximal-most end of the connection body and a proximal end of one of the containing grooves.

15. The stent delivery system according to claim 14, wherein the protector is positioned between the outer surface of the inner tube and the inner surface of the housing.

16. The stent delivery system according to claim 14, wherein the protector possesses an inner surface and an outer surface, the outer surface of the inner tube contacting the inner surface of the protector when the connection body is moved axially towards the proximal-most end of the inner tube.

17. The stent delivery system according to claim 16, wherein the housing possesses an inner surface and an outer surface, the outer surface of the protector moving towards the inner surface of the housing when the connection body is moved axially towards the proximal-most end of the inner tube.

18. The stent delivery system according to claim 14, wherein the protector comprises a first slide member and a second slide member, the first slide member being connected to the proximal-most end of the connection body and being configured to move towards the second slide member when the connection body is moved axially towards the proximal-most end of the inner tube.

* * * * *